United States Patent [19]

Beidler et al.

[11] Patent Number: 4,528,395

[45] Date of Patent: Jul. 9, 1985

[54] PROCESS FOR ESTERIFYING 3,5-DI-TERT-BUTYL-4-HYDROXYBENZOIC ACID

[75] Inventors: Richard F. Beidler, Marietta, Ohio; Philip R. Ruby, Millington, N.J.

[73] Assignee: American Cyanamid Co., Stamford, Conn.

[21] Appl. No.: 523,303

[22] Filed: Aug. 15, 1983

[51] Int. Cl.³ ............................................. C07C 69/88
[52] U.S. Cl. .................................................. 560/067
[58] Field of Search ......................................... 560/067

[56] References Cited

FOREIGN PATENT DOCUMENTS 2421309 11/1974 Fed. Rep. of Germany ........ 560/25

Primary Examiner—Paul J. Killos
Attorney, Agent, or Firm—Steven J. Hultquist

[57] ABSTRACT

A process for making $C_8$–$C_{20}$ alkyl esters by esterification of 3,5-di-tert-butyl-4-hydroxybenzoic acid with a $C_8$–$C_{20}$ alcohol. The esterification reaction is conducted at 110°–150° C. in the presence of 5–20 weight percent based on the weight of 3,5-di-tert-butyl-4-hydroxybenzoic acid, of a strongly acidic gel-type ion-exchange resin catalyst having less than about 8 percent crosslinking.

11 Claims, No Drawings

PROCESS FOR ESTERIFYING 3,5-DI-TERT-BUTYL-4-HYDROXYBENZOIC ACID

This invention generally relates to an improvement in the esterification of 3,5-di-tert-butyl-4-hydroxybenzoic acid with a $C_8$–$C_{20}$ alcohol to form the corresponding ester. More particularly, it relates to an improved process for the preparation of hexadecyl 3,5-di-tert-butyl-4-hydroxybenzoate.

The preparation of higher alkyl esters of 3,5-di-tert-butyl-4-hydroxybenzoic acid by the acid-catalyzed reaction of 3,5-di-tert-butyl-4-hydroxybenzoic acid with a $C_8$–$C_{20}$ alcohol is well-known in the art. Esterification catalysts such as sulfuric acid, methanesulfonic acid, and p-toluenesulfonic acid are exemplary of the conventional acid catalyst materials used to prepare such esters in high yields. However, these acid catalysts suffer from the deficiency that they are corrosive and cannot be recycled.

The acid catalysis of esterification reactions between alcohols and carboxylic acid by means of non-corrosive, recyclable ion-exchange resins is also well-known. While macroreticular resins containing sulfonic acid groups, such as Amberlyst®15 (Rohm & Haas Company), are normally excellent esterification catalysts, large yield losses occur when 3,5-di-tert-butyl-4-hydroxybenzoic acid is used, due to debutylation of the reaction product.

There is a need, therefore, for a recyclable, non-corrosive catalyst and for a process that will provide high yields of esters of 3,5-di-tert-butyl-4-hydroxybenzoic acid with low levels of debutylation of the esterification reaction product.

The present invention provides an improvement in a process for preparing $C_8$–$C_{20}$ alkyl esters of 3,5-di-tert-butyl-4-hydroxybenzoic acid wherein the 3,5-di-tertbutyl-4-hydroxybenzoic acid is reacted with a $C_8$–$C_{20}$ alcohol, at an elevated temperature, in the presence of a strongly acidic ion-exchange resin catalyst, to form the desired ester. The improvement comprises using about 5-20% by weight, based on the weight of the 3,5-di-tert-butyl-4-hydroxybenzoic acid, of a strongly acidic gel-type ion-exchange resin catalyst having less than 8% cross-linking and carrying out the reaction at a temperature in the range of from about 110° to about 150° C. to effect esterification.

In a preferred embodiment, the gel-type ion-exchange exchange resin catalyst has 1-4% cross-linking, and the reaction is conducted at a temperature from about 130° to about 140° C.

In an especially preferred embodiment, a $C_{12}$–$C_{18}$ alcohol is employed as the alcohol reactant.

The improved process of this invention provides the desired ester in high yields with minimal debutylation.

The term "strongly acidic ion-exchange resin catalyst," as used herein, is defined as an ion-exchange resin containing sulfonic acid functionality.

The term "gel-type ion-exchange resin," as used herein, is defined as a cross-linked resin in which the ions to be exchanged must diffuse through a gel structure to the exchange sites. The gel-type ion-exchange resin has a porosity which is usually below 40 Angstrom units, as compared to the macroreticular-type resin which has a much larger pore size. The macroreticular-resin does not give as high a yield of the desired ester as the gel-type resin provides. The macroreticular resin also causes a higher degree of debutylation of the benzene ring.

The gel-type ion-exchange resins which usefully may be employed as catalysts in the broad practice of the present invention include sulfonated copolymers of styrene and divinylbenzene. The styrene and divinylbenzene are copolymerized in amounts which may vary depending on the degree of cross-linking desired. If, for example, 8% cross-linking is desired, 8% by weight of divinylbenzene, based on the weight of styrene, is copolymerized with the styrene prior to subsequent sulfonation of the cross-linked resin. The gel-type ion-exchange resins employed in the present invention contain less than 8% cross-linking, preferably about 1-4% cross-linking. Illustrative examples of suitable strongly acidic gel-type ion-exchange resins include Dowex® 50WX2-100, and Dowex® 50WX2-400 (Dow Chemical Company), and Lewatit SC-102 (Bayer AG).

The amount of ion-exchange resin catalyst which usefully may be employed ranges from about 5 to 20% by weight, preferably from about 8 to 12% by weight, based on the weight of 3,5-di-tert-butyl-4-hydroxybenzoic acid employed.

The amount of $C_8$–$C_{20}$ alcohol employed in the esterification reaction is preferably from about 1.08 to about 1.10 moles per mole of 3,5-di-tert-butyl-4-hydroxybenzoic acid present in the reaction mixture.

Illustrative examples of suitable alcohols include 1-octanol, 2-octanol, 1-dodecanol, 1-hexadecanol, 1-octadecanol, and the like. The preferred alcohol is 1-hexadecanol.

The esterification preferably is carried out in an inert solvent having a boiling point from about 110° to about 150° C., most preferably from about 130° to about 140° C. Suitable solvents include toluene, xylene, and mixtures thereof.

The esterification reaction is suitably conducted with stirring of the reaction mixture at reflux temperature, with removal of water, until the esterification is completed. The catalyst may then be separated by conventional means and rinsed with inert solvent to provide for re-use of the catalyst. Wash liquor may then be added to the reaction mixture and solvent removed under vacuum. The melt may then be cooled to about 70° C. and added to cold (5° C.) methanol. After aging at 10° C., the crystals may be recovered by conventional means, washed with cold (5° C.) methanol and dried.

The following examples are illustrative of the present invention. All parts and percentage are by weight unless otherwise indicated.

EXAMPLE 1

PREPARATION OF HEXADECYL 3,5-DI-TERT-BUTYL-4-HYDROXYBENZOATE

To a 1-liter round bottom flask equipped with a stirrer, thermometer, and Dean-Stark water separator are added 3,5-di-tert-butyl-4-hydroxybenzoic acid (150.0 grams; 0.60 mole), 1-hexadecanol (157.7 grams; 0.65 mole), toluene (125 mls) and 15.0 grams of dried Dowex® 50 WX2-100 (acid equivalents=2 eq./liter; 2% cross-linking) as catalyst. The mixture is stirred at reflux for 11 hours to remove by-product water, and filtered to remove the catalyst. The catalyst is then washed with toluene, the washing is added to the reaction mixture filtrate, and the filtrate is vacuum stripped, under 25 inches of mercury, to a temperature of 150° C. The melt is cooled to 70° C. and added to 2000 mls of cold (5° C.)

methanol. The resulting mixture is stirred and cooled to below 10° C., then filtered to remove the insoluble crystals. The filter cake is washed with cold (5° C.) methanol, and dried to obtain 265 grams (93.5% of theoretical) of the desired product. Analysis of the product by high performance liquid chromatography shows less than 3% debutylation.

EXAMPLE 2

The procedure of Example 1 is followed in every detail except that Dowex® 50WX2-400 (acid equivalents=2 eq./liter; 2% cross-linking) is used as the catalyst, and the reaction mixture is refluxed for 14 hours. The desired product is obtained in a yield which is 93.3% of theoretical yield.

EXAMPLE 3

The procedure of Example 1 is followed in every detail except that 15.0 grams of dried Amberlyst® 15 (acid equivalents=1.8 eq./liter; 20% cross-linking) is substituted for the Dowex® 50WX2-100. The desired product is obtained in a yield which is only 59% of theoretical yield.

EXAMPLE 4

The procedure of Example 1 is followed in every detail except that 15.0 grams of Amberlite® IR-120 Plus, which is about 8% cross-linked, and has an acid equivalents content of 1.9 eq./liter, is substituted for the Dowex® 50WX2-100. After heating for 4 days, only 50% of the theoretical by-product water is obtained, indicating a yield of product of only 50% of theoretical yield.

What is claimed is:

1. In a process for making a $C_8$–$C_{20}$ alkyl ester from 3,5-di-tert-butyl-4-hydroxybenzoic acid by reaction of 3,5-di-tert-butyl-4-hydroxybenzoic acid with a $C_8$–$C_{20}$ alcohol at elevated temperature in the presence of a strongly acidic ion-exchange resin catalyst, the improvement comprising employing as said acidic ion-exchange resin catalyst from 5 to 20 percent by weight, based on the weight of the 3,5-di-tert-butyl-4-hydroxybenzoic acid, of a strongly acidic gel-type ion-exchange resin catalyst having less than about 8 percent cross-linking, and conducting the reaction of 3,5-di-tert-butyl-4-hydroxybenzoic acid with said $C_8$–$C_{20}$ alcohol at 110° to 150° C.

2. A process according to claim 1 wherein said strongly acidic gel-type ion-exchange resin catalyst has 1 to 4 percent cross-linking.

3. A process according to claim 1 wherein said reaction of 3,5-di-tert-butyl-4-hydroxybenzoic acid with said $C_8$–$C_{20}$ alcohol is conducted at 130° to 140° C.

4. A process according to claim 1 wherein 3,5-di-tert-butyl-4-hydroxybenzoic acid is reacted with a $C_{12}$–$C_{18}$ alcohol.

5. A process according to claim 1 wherein said strongly acidic gel-type ion-exchange resin catalyst comprises a sulfonated copolymer of styrene and divinylbenzene.

6. A process acccording to claim 1 wherein said strongly acidic gel-type ion-exchange resin catalyst is employed in said reaction of 3,5-di-tert-butyl-4-hydroxybenzoic acid with said $C_8$–$C_{20}$ alcohol at concentration of 8 to 12 percent by weight, based on the weight of 3,5-di-tert-butyl-4-hydroxybenzoic acid.

7. A process according to claim 1 wherein concentration of said $C_8$–$C_{20}$ alcohol in said reaction is from about 1.08 to about 1.10 moles of alcohol per mole of 3,5-di-tert-butyl-4-hydroxybenzoic acid.

8. A process according to claim 1 wherein said $C_8$–$C_{20}$ alcohol is selected from the group consisting of 1-octanol, 2-octanol, 1-hexadecanol, 1-octadecanol, and mixtures thereof.

9. A process according to claim 1 wherein said reaction is conducted in a substantailly inert solvent medium having a normal boiling point of from about 110° to about 150° C.

10. A process according to claim 9 wherein said solvent medium is selected from the group consisting of toluene, xylene, and mixtures thereof.

11. A process according to claim 1 wherein said alkyl ester is hexadecyl 3,5-di-tert-butyl-4-hydroxybenzoate.

* * * * *